United States Patent [19]

Lia et al.

[11] Patent Number: 5,061,995
[45] Date of Patent: Oct. 29, 1991

[54] APPARATUS AND METHOD FOR SELECTING FIBER OPTIC BUNDLES IN A BORESCOPE

[75] Inventors: Raymond A. Lia; Michael Kehoskie, both of Auburn; Richard A. Kokosa, Skaneateles, all of N.Y.

[73] Assignee: Welch Allyn, Inc., Skaneateles Falls, N.Y.

[21] Appl. No.: 573,870

[22] Filed: Aug. 27, 1990

[51] Int. Cl.[5] ............................ H04N 7/18; A61B 1/6; G02B 6/6

[52] U.S. Cl. .......................................... 358/98; 128/6; 385/117

[58] Field of Search ............... 358/98, 225; 350/96.25, 350/96.26; 128/4, 6

[56] References Cited

U.S. PATENT DOCUMENTS 4,272,156  6/1981  Ishibashi et al. ............... 350/96.26
4,802,460  2/1989  Ohkuwa et al. .................. 128/6
4,827,909  5/1989  Kato et al. ...................... 358/98
4,980,763  12/1990  Lia .................................. 358/98

Primary Examiner—Tommy P. Chin
Assistant Examiner—Michael H. Lee
Attorney, Agent, or Firm—Wall and Roehrig

[57] ABSTRACT

Two or three fiber optic cables, each adapted for a particular purpose is provided in the insertion tube of an endoscope/borescope for illuminating an object to be viewed. The proximal end of the insertion tube is positioned adjacent a source of light. A device is provided for rotating the proximal end of the insertion tube to position one or more of the fiber optic bundles in optical alignment with the source of light to illuminate the object to be viewed with the desired light. Alternatively, an individual bundle can be illuminated by insertion in a proper receptacle in an interconnecting module positioned in optical alignment with a light source.

15 Claims, 3 Drawing Sheets

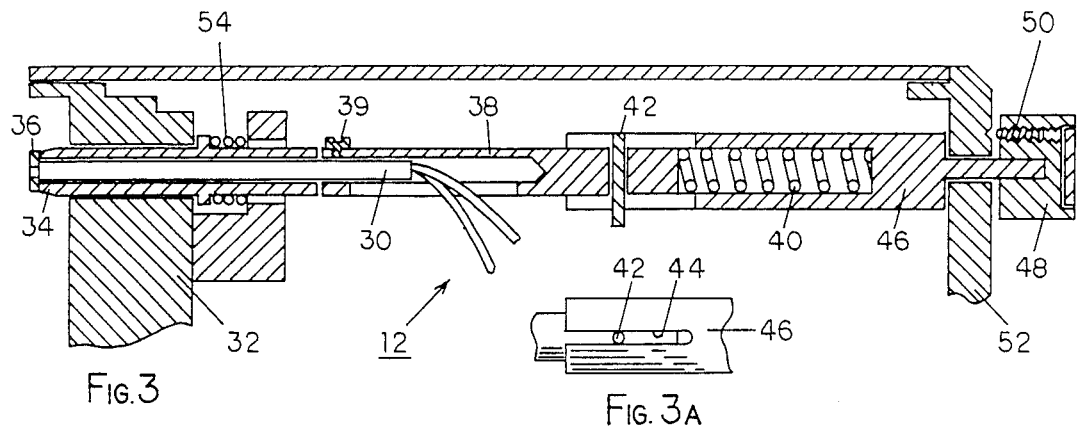
Fig.3　Fig.3A
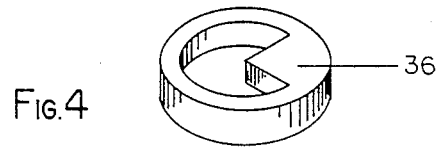
Fig.4
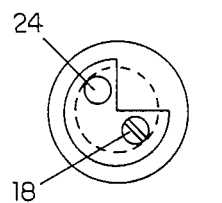 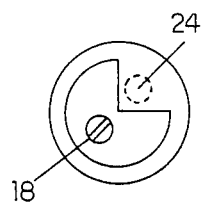 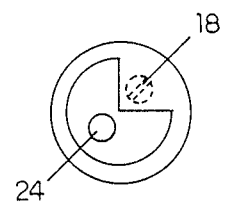
Fig.5A　Fig.5B　Fig.5C
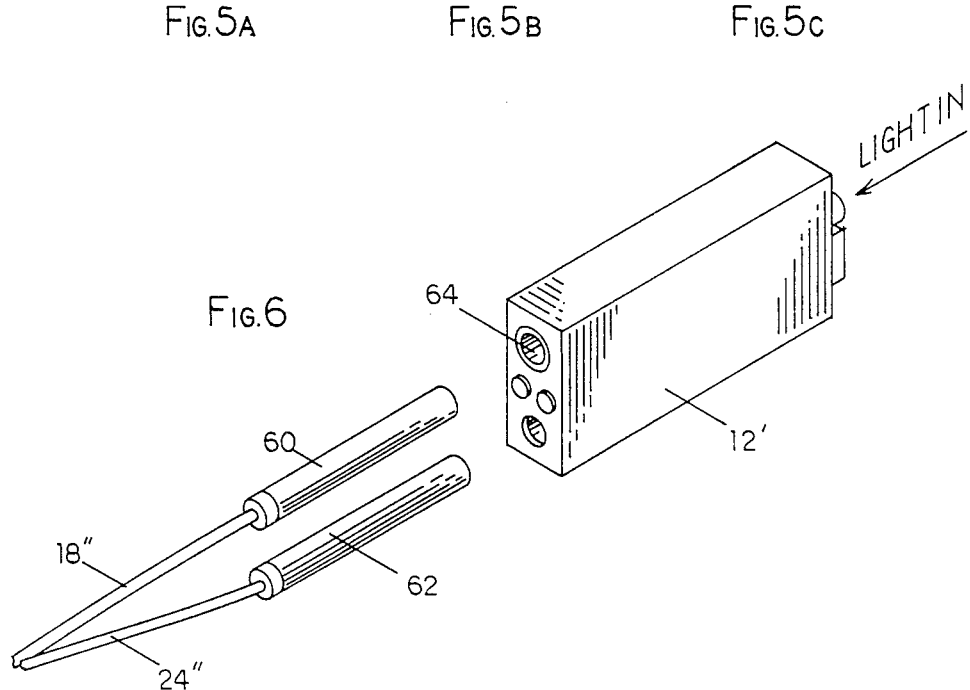
Fig.6

APPARATUS AND METHOD FOR SELECTING FIBER OPTIC BUNDLES IN A BORESCOPE

BACKGROUND OF THE INVENTION

This invention relates to borescopes/endoscopes having an elongated insertion tube with a video pickup device at the distal end thereof. More particularly, this invention relates to a borescope/endoscope having means for measuring the various parameters of an object being viewed on a video pickup display screen.

For many years now, borescopes/endoscopes of the type having an elongated insertion tube with a video pickup at the distal end for viewing remotely located targets have been common devices in the art. More recently, means for measuring dimensions and other parameters of the object being viewed have been proposed which permit measurements without the necessity of providing a scale or a known spacing of the end of the video probe from the object being viewed. Typical of this type of device are co-pending applications assigned to the common assignee of the present case entitled System for Measuring Objects Viewed Through a Borescope, Ser. No. 364, filed June 12, 1989 now U.S. Pat. No. 4,980,763, issued Dec. 25, 1990 and Video Measurement With Automatic Distortion and Calibration, Ser No 506,175 filed Apr. 9, 1990 (050).

According to these applications, in order to measure an object, an image or shadow having a known characteristic is projected onto the object being viewed. Variations in the known characteristics of the shadow are used to calibrate the measurement of the dimensions of the object being viewed. In certain applications where it is desired to measure the characteristics of the object being viewed, it is also desirable to view the object without the interference of a shadow or other auxiliary characteristic being projected onto the object being viewed.

OBJECTS AND SUMMARY OF THE INVENTION

Accordingly, it is an object of the present invention to provide a video borescope of the type used for measuring parameters of the object being viewed in which the shadow or other image parameter used to determine distance to the object can be selectively eliminated.

It is another object of the present invention to provide a borescope for measuring parameters of the object being viewed in which the measurement system can be selectively disabled.

It is a still further object of the present invention to provide a borescope/endoscope, having a video pickup at the distal end of an insertion tube, with an object illumination system in which the illumination can be selectively maximized to view selected parameters of the object to be viewed.

In a preferred embodiment of the present invention an object illumination system is provided in which the object to be viewed may be illuminated by light transmitted through at least two separate fiber optic illumination bundles, one of which does not have any shadow projection means therein. Means are provided for selectively illuminating one or the other or both of the fiber optic bundles, depending on the illumination desired on the object to be viewed.

BRIEF DESCRIPTION OF THE DRAWING

FIG. 3 is a cross sectional view with parts broken away of a mechanism for selectively positioning one or the other or both fiber optic bundles in optical alignment with a light source;

FIG. 3A is a fragmentary view of a portion of the tube 46 of FIG. 3;

FIG. 4 is a perspective view of an aperture plate mounted on the end of the device of FIG. 3;

FIGS. 5A, 5B, and 5C show an end view from the left hand end of FIG. 3 wherein the fiber optic bundle cylinder has been rotated to expose one or the other or both of the fiber optic bundles;

FIG. 6 is a perspective view of another embodiment of the present invention.

DETAILED DESCRIPTION OF THE PREFERRED EMBODIMENT

Figure 1:
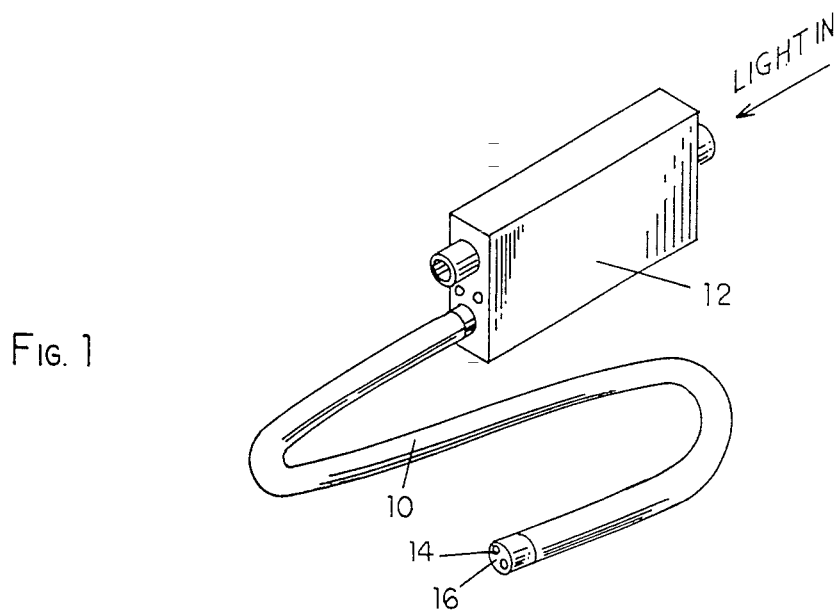
FIG. 1 is a perspective view of an insertion tube connected to an interface unit embodying the present invention.

As shown in FIG. 1, an insertion tube 10 is connected to an interface module 12 and carries in the distal end a video pick up 14 and fiber optic illumination assembly 16. The video pick up 14 is connected through tube 10 and module 12 to the video camera display circuitry, not shown, in the borescope/endoscope control package. The fiber optic assembly 16 includes a shadow bar 22 and a pair of fiber optic bundles 18 and 24 that extend from the distal end thereof to the proximal end connected to interface module 12, as will be described in more detail herein.

Figure 2A:
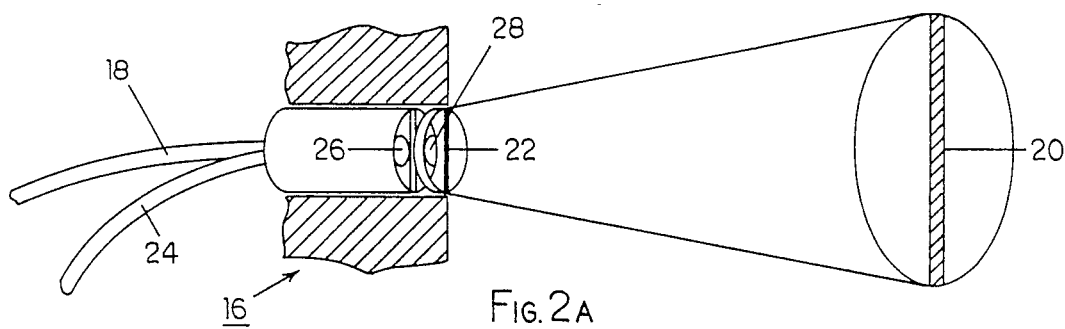
FIG. 2A is a perspective view of the distal end of the fiber optic bundles according to the present invention showing the measurement bundle illuminated to form a shadow projected on the object to be viewed.
Figure 2B:
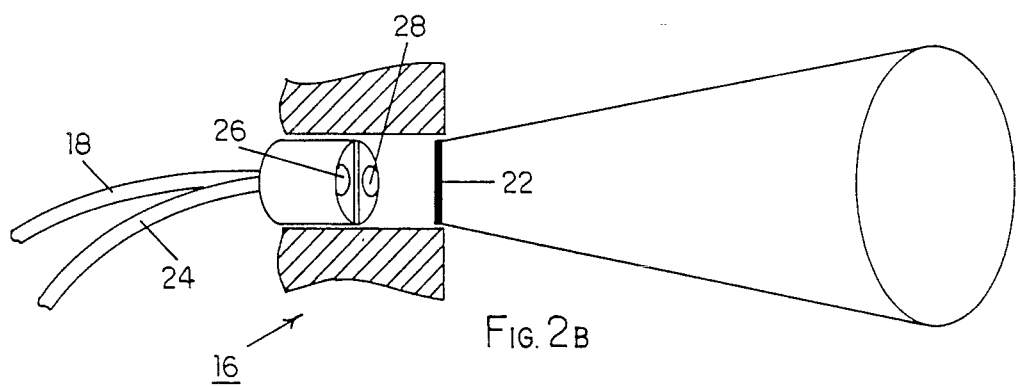
FIG. 2B is a perspective view of the distal end of the fiber optic bundle showing the other fiber optic bundle being illuminated without any shadow being projected on the object.

Referring now to FIGS. 2A and 2B, to measure parameters of an object being viewed, one method for accomplishing this has been to project an illumination pattern having a shadow on the object being viewed in such a way that the shadow is displaced from an initial starting point in proportion to the distance the object being viewed is from the video pickup lens system. This has typically, in the foregoing applications, taken the form of a fiber optic bundle 18 for illuminating the object. Bundle 18, in one form, is flattened to an elongated flat strip and a shadow bar 22 is mounted adjacent the distal end of bundle 18 so as to project a shadow on the object being illuminated. When light is projected on the proximal end of the bundle 18, light is transmitted through the bundle and is projected onto the object to be viewed. In FIG. 2A the object illumination pattern includes a distinct linear shadow 20 cast on the object being viewed. To accomplish this, the flattened fiber optic bundle 18 has, at its distal end a small shadow bar 22 just in front of the fiber optic bundle, displaced from the axis thereof, so as to create the aforesaid shadow on the object to be viewed. In measuring parameters of the object being viewed, the magnification of the lens system can be determined from the displacement of this shadow on the object being viewed from an initial zero point.

As shown in FIG. 2B, in addition to providing the narrow elongated fiber optic bundle 18 and its associated shadow bar 22, a second fiber optic bundle 24 is provided. Bundle 24, is split into two portions 26 and 28 at its distal end. Ends 26 and 28 are formed into partial circles positioned on either side of the narrow rectangular cross-sectional end of the first fiber optic bundle 18. Light from ends 26 and 28 will flood the object to be viewed when bundle 24 is illuminated. The bundle 24 provides illumination of the object to be viewed without any shadow (FIG. 2B when the second fiber optic bundle 24 is energized.

In use, when a measurement is to be made, bundle 18 only will be illuminated and a shadow will be projected onto the object to be viewed. If it is desired to view the object without a shadow, bundle 24 is illuminated. In some cases, additional illumination may be required and then both bundles will be simultaneously illuminated. The shadow will basically be overcome by the illumination of bundle 24 and the rest of the illumination of bundle 18 will add to that of bundle 24 to "light up" the object to be viewed to the maximum possible.

Referring now to FIG. 3, there is shown a mechanism for rotating the proximal end of a fiber optic tube 30 in which is located the proximal end of both fiber optic bundles 18 and 24 described in connection with FIG. 2. These bundles, at their proximal ends are generally cylindrical in cross-section and are spaced apart a distance sufficient so that they can be individually aligned with a source of illumination without accidentally illuminating both fiber optic bundles. As may be seen in FIG. 3, this generally involves an interface module 12 which has a frame portion 32 in which is fixed a cylindrical tube 34 which has mounted on the end thereof an aperture plate 36 as is shown in FIGS. 3 and 4. Rotatably mounted within the tube 34 is a second tube 30 containing the encapsulated proximal ends of fiber optic bundles 18 and 24 as described above in FIGS. 2A and 2B. This tube 30 is secured in an extension tube 38 by a set screw 39. Tube 38 is spring loaded to the left-hand position shown in FIG. 3 by spring 40. Referring to FIG. 3A, pin 42 is fixed in tube 38 and extends into the slot 44 of a larger tube 46 which at its right hand end carries an actuating knob 48. The knob 48 has detente pin 50 positioned to accurately align the tube 46 in one of three pre-selected positions by positioning the detente in corresponding recesses in the outer face plate 52 of the inter-connecting module 12. The module 12 is adapted to be plugged into the electronic package of a borescope/endoscope according to the present invention and the tube 34 which is fixed against rotation within the frame 32 is spring urged to the left by spring 54 into proper optical contact and alignment with a light source in the electronics package, not shown. The fiber optic bundles 18 and 24 extend out of the tube 30 and module 12 through the insertion tube 10 to the distal end thereof and are encapsulated therein as shown in FIG. 2.

In operation, the interface module is mounted on the electronics package and clamped in position. By rotating knob 48, tube 46 is rotated, which in turn, through pin 42, rotates tube 38 which has fixed therein tube 30. The two fiber optic bundles 18 and 24 are encapsulated in the tube 30 and can be rotated plus or minus approximately ninety degrees, see FIG. 5A, 5B and 5C to bring into optical alignment with a light source either fiber optic bundle 18, fiber optic bundle 24, or both. This is shown diagrammatically in FIG. 5 in which the three possible combinations are shown. This allows the investigator to selectively position the desired fiber optic bundle in alignment with the light source to provide the particular illumination of the object to be viewed that is best suited for the purpose at hand.

Figure 7A:
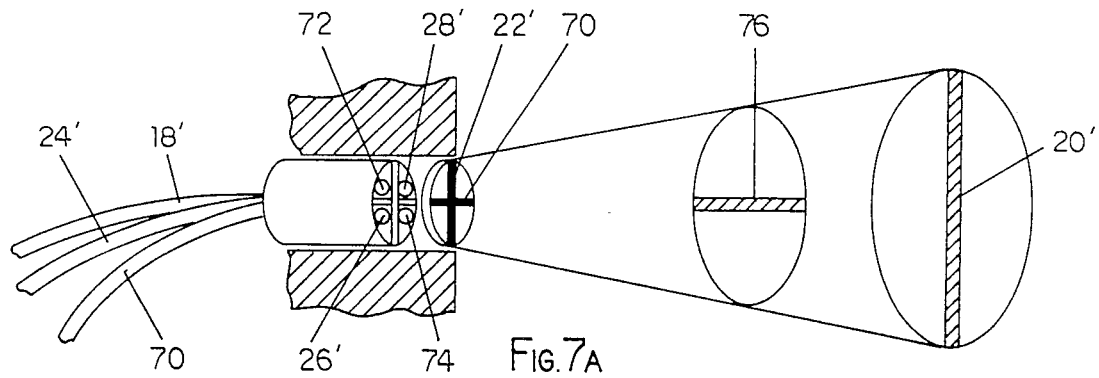
FIGS. 7A and 7B are similar to FIGS. 2A and 2B of another embodiment of the present invention.
Figure 7B:
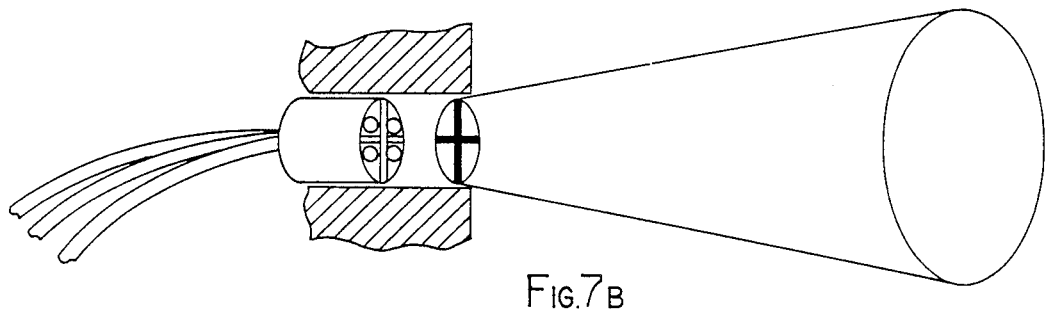
Figure 8A:
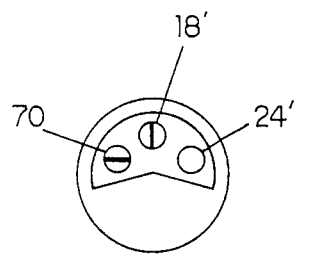
FIGS. 8A, 8B, and 8C are views similar to FIG. 5 showing the embodiment of FIG. 7.
Figure 8B:
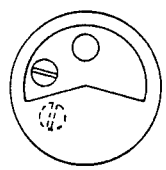
Figure 8C:
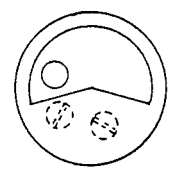

Referring now to FIGS. 7 and 8, there is shown another embodiment of the present invention. In this embodiment, the insertion tube carries three fiber optic bundles. Bundle 18' terminates in a flat strip like bundle 18 for forming the vertical shadow 20; with bar 22'. Bundle 70 is terminated at the distal end in a flat strip disposed at right angles to strip 18' to form in FIG. 7A a horizontal shadow 76 with bar 70. The end of strip 70 is divided to fit one half on either side of strip 18'.

Bundle 24' is divided into four sectors 26', 28', 72 and 74 which are disposed in the four quadrants about the crossed strips 18' and 70. These bundle segments, when illuminated at the proximal end, project uninterrupted light on the object resulting in essentially complete illumination of the object. The shadows 20' and 76 are not projected when only bundle 70 is illuminated, and when all three bundles are illuminated at the proximal ends, the shadows 20' and 76 are substantially washed out or eliminated.

When the proximal ends of the three bundles are encapsulated in a tube, the assembly may be rotated similarly to the tube 30 to expose one, two or three bundles to the source of illumination at the interface module 12.

We thus provide, in this embodiment the capability to project one or two shadows disposed at 90° to each other, completely clear light from the four sectors or a combination of any two or more of the above.

Referring now to FIG. 6, there is shown another embodiment of the present invention in which instead of providing an encapsulated cylindrical module for rotation so as to align optically one or more of the fiber optic bundles, the individual bundles 18" and 24" are encapsulated in cylindrical tubes 60 and 62. In the embodiment of FIGS. 7 and 8 bundle 70 would also be encapsulated in a tube. The inter-face module 12' is then configured with a receptacle 64 suitable for receiving one of the optical fiber bundle tube encapsulated ends, as may be desired to project the proper illumination at the distal end of the insertion tube. This embodiment requires the insertion of the selected encapsulated fiber optic bundle proximal end into the inter-face module for proper positioning within receptacle 64 so as to receive the illumination necessary to illuminate the object to be viewed. In this way, one or the other of the fiber optic bundles will be illuminated and the object will be illuminated in the desired fashion. In this embodiment, only one fiber optic bundle can be illuminated at a time.

Thus, a simple, economical and easy to use device has been provided for extending the operational utility of a borescope/endoscope of the type used to measure parameters of the object being viewed by projecting a shadow or other image on the object being viewed.

While this invention has been explained with reference to the structure disclosed herein, it is not confined to the details as set forth and this application is intended to cover any modifications and changes as may come within the scope of the following claims.

What is claimed is:

1. A borescope/endoscope having an elongated insertion tube with an image pickup in the distal end for viewing remotely located objects including:
   a first fiber optic bundle extending from the proximal to the distal end of said elongated insertion tube;
   at least one additional fiber optic bundle extending from the proximal to the distal end of said elongated insertion tube;
   said fiber optic bundles being adapted to transmit light from light source located adjacent the proximal ends thereof to the distal ends;
   the distal ends of said fiber optic bundles being configured to project at least two different levels of illumination upon the object to the viewed; and
   means for selectively positioning the proximal end of at least one of said fiber optic bundles in operational alignment with the light source mounted adjacent the proximal end of said insertion tube to illuminate the object to be viewed at the selected illumination level.

2. A borescope/endoscope having an elongated insertion tube with an image pickup in the distal end for viewing remotely located objects including:
   a first fiber optic bundle extending from the proximal to the distal end of said elongated insertion tube;
   at least one additional fiber optic bundle extending from the proximal to the distal end of said elongated insertion tube;
   said fiber optic bundles being adapted to transmit light from a light source located adjacent the proximal ends thereof to the distal ends;
   the distal ends of said fiber optic bundles being formed into different shapes with said first fiber optic bundle being formed into a narrow strip having a length substantially greater than the width; and
   means for selectively positioning the proximal end of at least one of said fiber optic bundles in operational alignment with the light source mounted adjacent the proximal end of said insertion tube to illuminate the object to be viewed at a selected illumination level.

3. The borescope/endoscope of claim 2 wherein the distal end of said second fiber optic bundle is formed into a pair of separate bundles each having a partially circular cross section.

4. The borescope/endoscope of claim 1 wherein said means for selectively positioning the proximal end of at least one of said fiber optic bundles in operational alignment with the light source includes an aperture plate having an opening adapted to permit said first, another or both bundles to receive illumination from the adjacent light source at the proximal end of said insertion tube.

5. The borescope/endoscope of claim 3 further including means for mounting the proximal ends of said first and second fiber optic bundles adjacent the light source, and means for rotating the proximal ends of said bundles to selectively position one or both of said ends in optical alignment with the light source.

6. The borescope/endoscope of claim 3 wherein the proximal and distal end of each of said fiber optic bundles are encapsulated in one or more cylindrical tubes and said means for selectively positioning said proximal ends in alignment with a light source includes:
   a cylindrical housing, mounted adjacent the source of light;
   a proximal cylindrical tube mounted for rotary movement therein and having encapsulated therein the proximal ends of said first and additional fiber optic bundles;
   a plate fixed on one end of said cylindrical housing having an aperture therein; and
   a shaft member operatively connected to said proximal cylindrical tube at one end and having knob means mounted on the other end
   so that by rotating said knob means the proximal end of at least one of the fiber optic bundles may be positioned in optical alignment with said aperture and the light source to transmit light to the distal end of said at least one fiber optic bundle.

7. The borescope/endoscope of claim 6 wherein said aperture plate and said means for rotating said cylindrical bundles in combination permit the optical alignment of the adjacent light source with one or more of said fiber optic bundles.

8. The borescope/endoscope of claim 1 wherein the proximal ends of said first and at least one additional fiber optic bundles are each encapsulated in a tube, and said means for selectively positioning said fiber optic bundle proximal ends in alignment with the light source includes a receptacle in optical alignment with the light source adapted to receive therein one of said tubes.

9. In a borescope/endoscope having an elongated insertion tube with a video imager in the distal end for viewing remotely located objects and measuring certain parameters thereof by projecting a shadow on the object, object illuminating means comprising:
   at least one fiber optic bundle extending from the proximal to the distal end of an insertion tube and having shadow forming means in said distal end;
   at least another fiber optic bundle extending from the proximal to the distal ends of said insertion tube having no shadow forming means therein;
   a light source mounted adjacent the proximal ends of said fiber optic bundles; and
   means for positioning at least one of said fiber optic bundle proximal ends in optical alignment with said light source.

10. The borescope/endoscope of claim 9 wherein said means for positioning one of said fiber optic bundle proximal ends includes means for simultaneously positioning all of said fiber optic bundle proximal ends in alignment with said light source.

11. Object illuminating means as described in claim 9 wherein:
   said means for positioning said fiber optic proximal ends include
   a frame member,
   a tubular receptacle in said frame member;
   an encapsulating tube containing the proximal ends of said fiber optic bundles rotatably mounted in said receptacle,
   spring means biasing said encapsulating tube and said tubular receptacle into optical alignment with a light source;
   knob and shaft members operatively connected to said encapsulating tube for rotating said tube within said receptacle, to move said fiber optic bundles into and out of optical alignment with the light source; and
   detente means operatively connected to said knob means to releasably secure said fiber optic bundles in a predetermined position relative to said light source.

12. In a borescope/endoscope having an elongated insertion tube with a video image pickup in the distal end for measuring parameters of remotely located objects using shadow projecting means, the method of illuminating an object comprising the steps of:
   providing a source of illumination;
   providing in an insertion tube at least one fiber optic bundle having shadow forming means adapted to project light and a shadow on the object to be viewed;
   providing in said insertion tube at least another fiber optic bundle without any shadow means adapted to project shadow free light on the object to be viewed;
   positioning the proximal end of said fiber optic bundles in said insertion tube adjacent said source of illumination; and
   selectively illuminating the proximal end of one of said fiber optic bundles to project to the distal ends thereof the desired illumination of to the object to be viewed.

13. The borescope/endoscope of claim 12 wherein the step of selectively illuminating the proximal end of one of said fiber optic bundles includes simultaneously illuminating the proximal end of at least two fiber optic bundles.

14. In a borescope/endoscope having an elongated insertion tube with a video imager in the distal end for viewing remotely located objects and measuring certain parameters thereof by projecting a shadow on the object, object illuminating means comprising:
   a first fiber optic bundle in an insertion tube extending from the proximal to the distal end thereof and having means at the distal end for forming a +first shadow line for projection onto the object to be viewed;
   a second fiber optic bundle in an insertion tube extending from the proximal to the distal end thereof and having means at the distal end for forming a second shadow line for projection onto the object to be viewed;
   said second line intersecting and being positioned at an angle to said first shadow line;
   a third fiber optic bundle in said insertion tube extending from the proximal to the distal end thereof having no shadow forming means;
   a light source mounted adjacent the proximal ends of said fiber optic bundle; and
   means for positioning said first, second and/or third fiber optic bundle in optical alignment with said light source.

15. The borescope/endoscope of claim 14 wherein said first and second shadow lines are disposed at right angles to each other.

* * * * *